US008309302B2

(12) United States Patent
Jaekel et al.

(10) Patent No.: US 8,309,302 B2
(45) Date of Patent: Nov. 13, 2012

(54) REAGENTS AND METHODS FOR PROCESSING BIOLOGICAL SAMPLES

(75) Inventors: Robert W. Jaekel, Deer Park, IL (US); Anna O'hare, Downers Grove, IL (US); Larry E. Morrison, Glen Ellyn, IL (US)

(73) Assignee: Abbott Laboratories, Abbott Park, IL (US)

( * ) Notice: Subject to any disclaimer, the term of this patent is extended or adjusted under 35 U.S.C. 154(b) by 269 days.

(21) Appl. No.: 11/485,901

(22) Filed: Jul. 13, 2006

(65) Prior Publication Data

US 2007/0048770 A1  Mar. 1, 2007

(51) Int. Cl.
  *C12Q 1/68* (2006.01)
  *G01N 1/30* (2006.01)
  *C07H 21/04* (2006.01)
  *C07K 5/00* (2006.01)

(52) U.S. Cl. ......... 435/6.1; 435/7.2; 435/40.5; 435/325; 536/23.1; 530/300

(58) Field of Classification Search .......... None
  See application file for complete search history.

(56) References Cited

U.S. PATENT DOCUMENTS

| | | | |
|---|---|---|---|
| 5,474,895 A * | 12/1995 | Ishii et al. | 435/6 |
| 5,500,339 A * | 3/1996 | Fuller et al. | 435/6 |
| 6,544,798 B1 * | 4/2003 | Christensen et al. | 436/177 |
| 2002/0128227 A1 * | 9/2002 | Hildreth | 514/58 |
| 2003/0022174 A1 * | 1/2003 | Visakorpi et al. | 435/6 |
| 2004/0029184 A1 * | 2/2004 | Gourevitch | 435/7.2 |
| 2005/0119201 A1 * | 6/2005 | Selker et al. | 514/44 |

OTHER PUBLICATIONS

Lewis et al "Sensitive in situ hybridization techniques using biotin-streptavidin-polyalkaline phosphatase complex" Journal of Clinical Pathology, 1987 40:163-166.*
Agulhon et al "Lysomoal amino acid transporter LYAAT-1 in teh rat central nervous system: An in situ hybridization an immunohistochemical study" Journal of Comparative Neurology, 2003 462: 71-89.*
Prestige Medical Series 2100 owners manual, Apr. 2001.*

* cited by examiner

*Primary Examiner* — Betty Forman
(74) *Attorney, Agent, or Firm* — Pierce Atwood LLP; Kevin M. Farrell; David J. Wilson

(57) ABSTRACT

Methods and processing reagents for improving washing and aging a biological sample in an assay are disclosed. The processing reagents comprise an aqueous base reagent and a low vapor pressure composition in sufficient amount to raise the boiling point of the base reagent. The methods comprise applying the base reagent and low vapor pressure composition to the biological sample for use at an elevated temperature.

11 Claims, No Drawings

REAGENTS AND METHODS FOR PROCESSING BIOLOGICAL SAMPLES

BACKGROUND OF THE INVENTION

Immunohistochemical (IHC) assays and assay techniques based on in situ hybridization (ISH) and, in particular, fluorescent in situ hybridization (FISH) are commonplace techniques used in medical diagnostics today. Biological samples such as tissue or cell samples from suspected or known diseased patients are analyzed using IHC and ISH/FISH techniques to determine or monitor the patient's status with respect to the disease under investigation. However, both IHC and ISH/FISH methods require the performance of numerous complex and time consuming steps in preparing the tissue and cell samples for and then carrying out the actual IHC or hybridization assay. When performed manually, these assay methods are tedious, technically demanding and time consuming. Nevertheless, well-established protocols have been established for manual assays.

As demand for both IHC and ISH/FISH assays has increased so also has the demand for automating these techniques to promote greater throughput, enhance reliability and spare technicians from the tedium and complexity of performing the assays. One artifact resulting from automation is the preferred use of smaller and more controlled amounts of sample and reagents in assay steps. For example, when FISH assays are performed manually sample washing, aging and pretreatment are typically performed using reagents in substantial excess such as dipping sample slides into Coplin jars filled with appropriate reagents. Much smaller reagent volumes (e.g., less than 1 ml) are highly desired for automated assays. Instrument designers are also keen to simplify assays for automated or semi-automated instrumentation.

FISH samples are typically treated in a buffered solution to accommodate digestion and/or washing. Such buffers typically include well-known buffers such as SSC (0.3M sodium chloride and 0.03M sodium citrate) or PBS (phosphate-buffered saline) at various concentrations. 2×SSC is typically used as a buffered post-hybridization wash reagent for formalin-fixed paraffin embedded (FFPE) tissue slides, and as a cell aging reagent for urine and amniotic fluid cell slides. Similarly, 0.4×SSC is typically used as a post-hybridization stringency wash for cell-based specimens. Wash reagents normally include a surfactant or detergent such as Nonidet P-40 (NP-40) to facilitate reagent spreading across the sample surface. Some investigators have found incubation of biological samples in high concentrations of glycerol in SSC (hot 2×SSC/50% glycerol) improves penetration of FISH probes in sample cells.

In an automated system, heating can be accomplished by placing a slide carrying the biological sample on the surface of a heating element. The biological samples are treated with reagents while the slide remains on the heating element. Assay reagents are usually applied mechanically. Many assay steps are performed at elevated temperatures. For example, in the Vysis PathVysion® HER-2 DNA Probe test breast tissue specimens are washed under stringent conditions following hybridization in a 2×SSC/NP-40 wash buffer at 73° C. for about 2 min or longer. However, assay steps at elevated temperatures can cause substantial evaporation of assay reagents. When small volumes are used, sample wash and aging steps and the resulting assay can be compromised by evaporation. Reagent evaporation has not been a concern in manual assays because sample slides are frequently covered during assay steps to prevent excess evaporation during the steps and Coplin jars or basins filled with excess reagents are used. For example, during the Vysis PathVysion® test, the cover slip is sealed to the sample slide using rubber cement to facilitate in situ hybridization. Following hybridization, the sealant is removed and the sample slide is immersed in wash buffer. Similarly, U.S. Pat. No. 6,855,559 to Christensen and U.S. Pat. No. 6,855,552 to Towne, et al. teach the use of the water immiscible LiquidCoverslip™ sold by Ventana Medical Systems to inhibit evaporation during automated IHC and ISH assays.

Designers of automated assays place a premium on the use of much smaller and more carefully controlled reagent volumes than are used in manual assays. Similarly, designers place a high premium on the ability to perform assay steps in an open and uncovered environment in contrast to the closed environment provided by a coverslip and the substantial excess of reagents required for performing them in a Coplin jar. Assaying small samples with small and tightly controlled reagent volumes in a closed environment presents substantial complexity for instrument designers that, understandably, is preferably avoided. In these circumstances, evaporation that results from assay steps at high temperature becomes much more difficult to control than in a manual assay using excess reagents and covered sample slides.

Non-ionic detergents such as Nonidet P-40 or NP-40 have traditionally been used with reagents to facilitate spreading the reagents evenly over the surface of a sample slide. However, new slide designs utilize hydrophobic barriers painted on the slides to allow better control of the sample test area but at the same time make control of reagent flow properties more important. It has been found that detergents such as NP-40, which have been desirable because they enhance the flow properties of assay reagents, may disadvantageously cause reagents to spread outside the hydrophobic barrier of a sample slide resulting in loss of reagent making an automated assay more difficult to control.

Accordingly, there is a need to identify new reagents and methods for washing and aging biological samples in IHC, ISH and FISH assays. Such new reagents and methods would enhance assay procedures by enabling assays to be performed at high temperatures with minimal reagent evaporation without incurring sample degradation, allowing reagents to be applied in smaller and more tightly controlled volumes and enabling other problematic materials such as detergents to be eliminated from assay steps.

SUMMARY OF THE INVENTION

The invention is based on the discovery that methods of washing or aging (i.e., processing) a biological sample for use in an assay can be substantially improved by applying a processing reagent to the sample, the processing reagent comprising an aqueous base reagent and a low vapor pressure composition in an amount sufficient to raise the boiling point of the base reagent. The amount of low vapor pressure composition is typically about 10% to about 40% by volume. The aqueous base reagent can be a buffered solution or other appropriate reagent. The low vapor pressure composition can be highly soluble in water and preferably is a water miscible reagent suitable for elevating the boiling point of the base reagent such as glycerol, propylene glycol and ethylene glycol, or mixtures thereof. It has been found that biological samples processed in an assay with such processing reagents are substantially more resistant to drying out when processed at elevated temperatures. For example, it has been found that buffered solutions such as SSC and water miscible reagents such as glycerol, propylene glycol or ethylene glycol are particularly useful for post-hybridization stringency washes.

SSC can be present in any strength such as 2×SSC and 0.4× SSC found useful for washing biological samples for FISH. The water soluble reagent is typically present in the range of about 10% to about 40% by volume. Preferably, the water soluble reagent is water miscible, and present in the range of about 15% to about 35%. Solutions of SSC and about 20% glycerol have been found especially useful. In another aspect of the invention, detergents such as NP-40 are excluded in the processing reagent.

DETAILED DESCRIPTION OF THE INVENTION

The invention provides improved methods and reagents for processing biological samples in immunohistochemical, in situ and fluorescent in situ hybridization, and other techniques requiring the biological samples to be processed at elevated temperatures without incurring the reagent loss that normally accompanies processing at elevated temperatures. The invention can be used beneficially in all processes where the biological samples are processed in aqueous reagents at temperatures greater than about 35° C. and more usefully at temperatures greater than about 40° C. or about 60° C. The processing reagents of the invention can be applied to the biological sample and the temperature of the reagent and sample raised for processing. The invention can be used generally for washing or aging the biological sample at elevated temperatures. The processing reagents and methods of the invention can be used manually but are especially useful in automated processes when tight control of reagent volumes and assay processing is desirable.

As used in the invention, a "biological sample" is a sample that contains cells or cellular material. Non-limiting examples of biological samples include urine, blood, cerebrospinal fluid (CSF), pleural fluid, sputum, peritoneal fluid, bladder washings, secretions (e.g., breast secretions), oral washings, tissue samples, touch preparations, or fine needle aspirates. The type of biological sample used in the methods of the invention will depend on the type of application one wishes to use (e.g., IHC, ISH and FISH and other methods requiring biological samples to be processed at elevated temperatures) and the type of disease one wishes to detect. For example, urine and bladder washings provide useful biological samples for the detection of bladder cancer and to a lesser extent prostate or kidney cancer using ISH/FISH assays. Pleural fluid is useful for detecting lung cancer, mesothelioma or metastatic tumors (e.g., breast cancer), and blood is useful for detecting leukemia.

A processing reagent of the invention comprises an aqueous base reagent and a low vapor pressure composition present in sufficient amount to raise the boiling point of the base solution. The base reagent can be a buffer solution or other reagent suitable for processing a biological sample in an assay. As used in the invention, a buffer solution is typically an aqueous solution intended to establish the pH of the solution in a particular range. Well known buffer solutions include SSC buffer, citrate buffer, Tris-HCl buffer, phosphate buffer (pH 6.0-8.0). More acidic and basic buffers are also known.

A low vapor pressure composition can be a reagent highly soluble in water and suitable for elevating the boiling point of the base reagent. Preferable low vapor pressure compositions are water miscible materials such as glycerol, propylene glycol and ethylene glycol or combinations thereof. Although the optimal concentration of the low vapor pressure composition in the base reagent will depend on the temperature and duration of sample processing to be performed, it has been found that concentrations in the range of about 10% to about 40% by volume are useful for processing biological samples in FISH and ISH assays. Concentrations of low vapor pressure composition in base reagent in the range of about 15% to about 35% are also useful. Concentrations of about 20% of low vapor pressure compositions such as glycerol and propylene glycol or combinations thereof in buffered solutions such as SSC are particularly useful in FISH assays.

As used in the invention, elevated temperature is intended to mean a temperature substantially above ambient. Typically, an elevated temperature of the invention is intended to mean above about 35° C. and more typically above about 40° C.

Surfactants or detergents such as NP-40 are also frequently used in processing reagents for IHC, ISH and FISH assays. However, these materials can cause excess reagent spreading over the surface of the slide thereby causing undesirable reagent loss from the sample and poor assay performance. It is desirable to reduce the amount of these materials or omit them entirely to reduce reagent spreading thereby reducing reagent loss and enabling better control and performance of the assay. It is an advantage of the invention, that surfactants and detergents can be omitted from the assay without compromising the assay. Therefore, in another aspect of the invention the surfactants and detergents are omitted from the processing reagent to reduce reagent loss due to spreading outside of the sample area e.g., defined by a hydrophobic barrier.

Fluorescent In Situ Hybridization

FISH assays can be performed on cells or tissue. When cells are used, the cells are typically harvested from a biological sample using standard techniques. For example, cells can be harvested by centrifuging a biological sample such as urine to form a cell pellet. The cells are then resuspended in phosphate-buffered saline (PBS). The cells can also be fixed, for example, in acid alcohol solutions, acid acetone solutions, or aldehydes such as formaldehyde, paraformaldehyde, and glutaraldehyde. For example, a solution containing methanol and glacial acetic acid in a 3:1 ratio can be used as a fixative. A neutral buffered formalin solution containing approximately 1% to 10% of 37-40% formaldehyde in an aqueous solution of sodium phosphate can also be used. Slides containing the cells can be prepared by removing a majority of the fixative, leaving the concentrated cells suspended in only a portion of the solution.

The cell suspension is applied to slides such that the cells do not overlap on the slide. Cell density can be measured by a light or phase contrast microscope. For example, cells harvested from a 20 to 100 ml urine sample typically are resuspended in a final volume of about 100 to 200 µl of fixative. Three volumes of the suspension (usually 3, 10, and 30 µl) are then dropped into 6 mm wells of a slide. The cellularity (density of the cells) in these wells is then assessed with a phase contrast microscope. If the well containing the greatest volume of cell suspension does not have enough cells, the cell suspension is concentrated and placed in another well.

Tissue samples are also obtained using standard techniques. For example, formalin fixed paraffin embedded breast tissue samples are cut into 4-6 µm thick paraffin sections using a microtome, mounted on a positively charged slide, and then fixed by baking overnight at 56° C.

Prior to FISH, chromosomal probes and chromosomal DNA contained within the cell each are denatured. Denaturation typically is performed by incubating in the presence of high pH, at elevated temperature (above about 70° C. to about 95° C.) with organic solvents such as formamide and tetraalkylammonium halides, or combinations thereof. For example, chromosomal DNA can be denatured by a combination of a temperature of about 73° C. and a denaturing buffer containing 70% formamide and 2×SSC. Denaturation conditions typically are established such that cell morphology is preserved. DNA probes can be denatured by heat. For example, probes can be denatured by heating to about 73° C. for about five minutes. Probes are allowed to anneal with the chromosomal DNA under hybridization conditions. "Hybridization conditions" are conditions intended to facilitate annealing between a probe and target chromosomal DNA. Hybridization conditions vary, depending on the concentrations, base reagent compositions, complexities and lengths of the probes, as well as salt concentrations, temperatures and length of incubation. The higher the concentration of probe, the higher the probability of forming a hybrid. For example, in situ hybridizations are typically performed in hybridization buffer containing 1-2×SSC, 50% formamide and blocking DNA to suppress non-specific hybridization. In general, hybridization conditions, as described above, include temperatures of about 25° C. to about 55° C., and incubation lengths of about 0.5 hours to about 96 hours. More typically, hybridization can be performed at about 32° C. to about 42° C. for about 2 to about 16 hours.

Non-specific binding of chromosomal probes to DNA outside of the target region can be removed by a series of washes. Temperature and concentration of salt in each wash depend on the stringency desired for the wash. For example, for high stringency conditions, washes can be carried out at temperatures from about 45° C. to about 80° C. using 0.2× to about 2×SSC, and about 0.1% to about 1% of a non-ionic detergent such as NP-40. Stringency can be lowered by decreasing the temperature of the washes or by increasing the concentration of salt in the washes.

IHC, ISH and FISH assays have been semi-automated and automated. For example, the Benchmark® and Discovery® instruments are available from Ventana Medical Systems and the Xmatrix system has recently been introduced by Biogenex. The methods and reagents of the invention are fully compatible with these instruments and require no special modification for implementation with them.

When performed with the Biogenex Xmatrix, for example, FISH samples are prepared as above on a barrier slide and inserted into the instrument. Wash reagents such as 2×SSC and NP-40 are applied to the samples automatically as the samples are processed. However, a substantial amount of reagent is likely to spread excessively beyond the sample area causing excessive evaporation as the sample is processed thereby degrading the quality of the resulting assay. It has been found, however, that addition of a low vapor pressure composition in sufficient amount to raise the boiling point of the buffer solution substantially reduces reagent evaporation and the consequent assay degradation that otherwise results. For example, glycerol, propylene glycol and ethylene glycol can be used as the low vapor pressure composition. When samples are washed or aged at elevated temperatures with a buffered solution of 2×SSC containing glycerol in a concentration range of about 10% to about 40%, reagent loss due to evaporation is substantially decreased. Preferably, glycerol is present in a concentration range of about 15% to about 35%. Such solutions are readily adaptable to automated instruments. An additional aspect of the invention is the elimination of detergents such as NP-40 from the reagent. This can reduce the spread of reagent outside of the sample area, e.g., as defined by the hydrophobic barrier and, correspondingly, reduce reagent loss due to evaporation.

EXAMPLES

The following non-limiting examples are provided by way of illustration only and are not intended to limit the invention in any manner. In the examples, all percentages listed are by volume for liquids and by weight for solids. The examples illustrate the methods and compositions of the invention as applied in FISH processing of peripheral blood lymphocytes or breast cancer tissue. The sample lymphocytes and cancer tissue were applied to 25 mm slides with a painted barrier for sample containment. The samples were aged, hybridized with FISH probes and washed after hybridization as described. The experiments were evaluated for loss of reagent due to spreading over the slide and evaporation, and assay performance. The slides were placed on a slide heater to maintain temperature control.

Known breast cancer tissue was prepared for hybridization with fluorescently labeled FISH probes for the Her-2 gene and a probe to enumerate the centromere of chromosome 17. The probes were obtained from Abbott Molecular Inc. (Des Plaines, Ill.) labeled with Spectrum-Orange and SpectrumGreen fluorescent labels. Peripheral blood lymphocytes were prepared for hybridization with a FISH probe to enumerate the centromere of chromosome 8. The probe was obtained from Abbott Molecular Inc. labeled with SpectrumOrange.

Example 1

Cell Aging with 2×SSC

Peripheral blood lymphocyte samples were aged using 2×SSC. For comparison, the lymphocytes were also aged with 2×SSC with 20% glycerol. About 700 µl reagent was applied to each sample slide and the slide was heated to 75° C. for about 5 min. Excess reagent was blown from the slide with an air knife. It was observed that some 2×SSC reagent was lost due to spreading beyond the slide barrier and most of the remaining reagent was lost due to evaporation. In contrast, it was observed that virtually none of the 2×SSC/20% glycerol reagent was lost due to spreading and again virtually none was lost due to evaporation. Thereafter, probe to enumerate the centromere of chromosome 8 was hybridized to the samples and further processed using conventional methodology. The assay performance for the 2×SSC sample was found to be average. The assay performance for the 2×SSC/20% glycerol sample was found to be very good.

Example 2

Post Hybridization Wash: Washing Tissue with 2×SSC

Breast cancer tissue slides were deparaffinized, pretreated, and hybridized with probes to HER2 and to enumerate chromosome 17 using conventional methodology. Thereafter, tissue slides were washed with 2×SSC with 0.3% NP-40. For comparison, tissue slides were washed with 2×SSC/20% glycerol in the absence of NP-40. About 500 µl reagent was applied to the sample slides and the slides were heated to 69° C. for about 1.5 min. Excess reagent was blown from the slides with an air knife. It was observed that most of the 2×SSC/NP-40 reagent was lost due to spreading beyond the slide barrier and most of the remaining reagent was lost due to evaporation. The assay performance was found to be poor. Signals were found to be non-specific and background was significant. In contrast, virtually none of the 2×SSC/20% glycerol reagent was lost due to spreading and again virtually none was lost due to evaporation. The assay performance was found to be very good.

Example 3

Post Hybridization Wash with 0.4×SSC

Peripheral blood lymphocyte samples were hybridized with FISH probe to enumerate the centromere of chromosome 8. Following hybridization, the coverslip was removed from the slide and the samples were subjected to a post-hybridization wash with 0.4×SSC/0.3% NP-40. For comparison, samples were also subjected to post hybridization wash with 0.4×SSC alone and 0.4×SSC with glycerol in amounts increasing up to 35% glycerol—all in the absence of NP-40.

Excess buffer was blown from the slides. The slides were heated at 45° C. for 30 sec to remove all remaining buffer from the slides. About 500 µl of 0.4×SSC/0.3% NP-40 wash solution was pipetted onto the slides inside the barrier. The slides were heated at 68° C. for 1.5 min. Excess reagent was blown off. DAPI stain was applied to the samples and a cover slip applied. Probe hybridization was observed using a fluorescent microscope.

The addition of about 10% or more glycerol to the wash reagent was found to improve the process dramatically. When the conventional 0.4×SSC/0.3% NP-40 reagent was used, substantial reagent was lost due to spreading and most of the remaining reagent was lost due to evaporation. Further, assay performance was poor with non-specific signals common and background significant. In contrast, when 0.4×SSC/20% glycerol was used without NP-40, virtually no reagent was lost due to spreading or evaporation and the assay performance was considered very good. Assay performance began to deteriorate as the glycerol concentration increased above 20%. Table 1 provides a summary of these results.

TABLE 1

Summary of Results for Post Hybridization Wash of peripheral blood lymphocyte samples. All samples were washed as described in Example 3 with 0.4XSSC with the indicated additives. The samples were evaluated for initial loss of reagent due to spreading, subsequent loss due to evaporation, and assay performance.

| Reagent Additive | Loss From Spreading | Loss From Evaporation | Assay Performance |
|---|---|---|---|
| 0.3% NP-40 | High | High | Poor[1] |
| — | Some | High | Poor |
| 5% Glycerol | Some | High | Poor |
| 10% Glycerol | Some | Some | Average |
| 15% Glycerol | Virtually None | Some | Good |
| 20% Glycerol | Virtually None | Virtually None | Very Good |
| 25% Glycerol | Virtually None | Virtually None | Good |
| 30% Glycerol | Virtually None | Virtually None | Average[2] |
| 35% Glycerol | Virtually None | Virtually None | Average[2] |

[1]Poor performance typically reflected the presence of non-specific signals and high background.
[2]Average performance typically reflected high background.

Other Embodiments

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A method for improving the processing of a paraffin-free or deparaffinized tissue or cellular sample for use in an assay at an elevated temperature by reducing evaporation of any processing reagent comprising applying to the sample a processing reagent applied in the absence of a detergent comprising an aqueous base reagent and a low vapor pressure composition consisting of glycerol at about 20% to about 25% and heating the sample to a temperature above about 35° C. to 75° C. while contacting said processing reagent.

2. The method for improving the processing of a sample of claim 1 wherein the base reagent comprises an aqueous buffer solution.

3. The method for improving the processing of a sample of claim 1 wherein the processing reagent is applied to the sample and the sample processed at a temperature above about 40° C.

4. The method for improving the processing of a sample of claim 1 wherein the aqueous base reagent comprises aqueous SSC.

5. A method for improving the processing of a paraffin-free or deparaffinized tissue or cellular tissue or cellular sample for use in an assay at an elevated temperature by reducing evaporation of any processing reagent comprising:
   a) providing: i) a tissue or cellular sample, ii) a processing reagent comprising an aqueous base reagent and a low vapor pressure composition selected from one or more of the group consisting of glycerol, ethylene glycol and propylene glycol, iii) an automated assay instrument;
   b) applying to the sample said processing reagent applied in the absence of a detergent and assaying said sample while contacting said processing reagent with said automated assay instrument at a temperature above about 35° C. to 75° C.

6. The method for improving the processing of a sample of claim 5 wherein the base reagent comprises an aqueous buffer solution.

7. The method for improving the processing of a sample of claim 5 wherein the processing reagent is applied to the sample and the sample processed at a temperature above about 40° C.

8. The method for improving the processing of a sample of claim 5 wherein the low vapor pressure composition is present in the reagent at a concentration in the range of about 10% to about 40% by volume.

9. The method for improving the processing of a sample of claim 5 wherein the low vapor pressure composition is present in the reagent at a concentration in the range of about 15% to about 35% by volume.

10. The method for improving the processing of a sample of claim 5 wherein the low vapor pressure composition is present in the reagent at a concentration in the range of about 20% to about 25% by volume.

11. The method for improving the processing of a sample of claim 5 wherein the aqueous base reagent comprises aqueous SSC.

* * * * *